(12) United States Patent
Gross

(10) Patent No.: US 8,862,243 B2
(45) Date of Patent: Oct. 14, 2014

(54) ELECTRICAL STIMULATION OF BLOOD VESSELS

(75) Inventor: Yossi Gross, Moshav Mazor (IL)

(73) Assignee: Rainbow Medical Ltd., Herzliya (IL)

( * ) Notice: Subject to any disclaimer, the term of this patent is extended or adjusted under 35 U.S.C. 154(b) by 1460 days.

(21) Appl. No.: 11/995,904

(22) PCT Filed: Jul. 25, 2006

(86) PCT No.: PCT/IL2006/000856
§ 371 (c)(1),
(2), (4) Date: Mar. 11, 2008

(87) PCT Pub. No.: WO2007/013065
PCT Pub. Date: Feb. 1, 2007

(65) Prior Publication Data
US 2008/0215117 A1    Sep. 4, 2008

Related U.S. Application Data

(60) Provisional application No. 60/702,491, filed on Jul. 25, 2005, provisional application No. 60/721,728, filed on Sep. 28, 2005.

(51) Int. Cl.
| | | |
|---|---|---|
| A61N 1/36 | (2006.01) | |
| A61N 1/32 | (2006.01) | |
| A61F 2/82 | (2013.01) | |
| A61F 2/06 | (2013.01) | |
| A61F 2/856 | (2013.01) | |
| A61N 1/05 | (2006.01) | |

(52) U.S. Cl.
CPC ............. *A61F 2/82* (2013.01); *A61F 2002/065* (2013.01); *A61N 1/326* (2013.01); *A61F 2250/0001* (2013.01); *A61F 2/856* (2013.01); *A61N 1/056* (2013.01); *A61N 1/36017* (2013.01)

USPC ................ 607/116; 607/2; 607/115; 607/119

(58) Field of Classification Search
USPC ........................ 607/2, 50, 115, 116, 118, 119
See application file for complete search history.

(56) References Cited

U.S. PATENT DOCUMENTS

| 3,650,277 A | 3/1972 | Sjostrand |
|---|---|---|
| 3,661,148 A | 5/1972 | Kolin |

(Continued)

FOREIGN PATENT DOCUMENTS

| EP | 0109935 | 5/1984 |
|---|---|---|
| EP | 0791341 | 8/1997 |

(Continued)

OTHER PUBLICATIONS

"Comparison of neurogenic contraction and relaxation in canine corpus cavernosum and penile artery and vein", Hayashida et al., Jpn. J. Pharmacol. 72:231-240 (1996). p. 232, col. 2, para 1; pp. 238, col. 2,para 2.

(Continued)

*Primary Examiner* — Carl H Layno
*Assistant Examiner* — Pamela M Bays
(74) *Attorney, Agent, or Firm* — Fish & Richardson P.C.

(57) ABSTRACT

Apparatus (20) is provided, including a bifurcation stent (50) comprising one or more electrodes (32), the stent (50) configured to be placed in a primary passage (52) and a secondary passage (54) of a blood vessel (30), and a control unit (34), configured to drive the electrodes (32) to apply a signal to a wall (36) of the blood vessel (30), and to configure the signal to increase nitric oxide (NO) secretion by the wall (36). Other embodiments are also described.

69 Claims, 3 Drawing Sheets

(56) References Cited

U.S. PATENT DOCUMENTS

| | | | |
|---|---|---|---|
| 4,154,227 A | 5/1979 | Krause et al. | |
| 4,201,219 A | 5/1980 | Bozal Gonzalez | |
| 4,474,630 A | 10/1984 | Planck et al. | |
| 4,692,148 A | 9/1987 | Kantrowitz | |
| 4,791,931 A | 12/1988 | Slate | |
| 4,809,681 A | 3/1989 | Kantrowitz | |
| 4,938,766 A | 7/1990 | Jarvik | |
| 5,192,271 A | 3/1993 | Kalb et al. | |
| 5,265,601 A | 11/1993 | Mehra | |
| 5,330,507 A | 7/1994 | Schwartz | |
| 5,411,031 A | 5/1995 | Yomtov | |
| 5,423,871 A | 6/1995 | Hoegnelid et al. | |
| 5,487,760 A | 1/1996 | Villafana | |
| 5,669,924 A | 9/1997 | Shaknovich | |
| 5,707,400 A | 1/1998 | Terry et al. | |
| 5,762,599 A | 6/1998 | Sohn | |
| 5,925,061 A | 7/1999 | Ogi et al. | |
| 5,967,986 A | 10/1999 | Cimochowski et al. | |
| 6,053,873 A | 4/2000 | Govari et al. | |
| 6,058,331 A | 5/2000 | King | |
| 6,086,527 A | 7/2000 | Talpade | |
| 6,120,520 A * | 9/2000 | Saadat et al. | 606/170 |
| 6,200,259 B1 | 3/2001 | March | |
| 6,277,078 B1 | 8/2001 | Porat et al. | |
| 6,347,247 B1 | 2/2002 | Dev et al. | |
| 6,445,953 B1 | 9/2002 | Bulkes et al. | |
| 6,463,323 B1 | 10/2002 | Conrad-Vlasak et al. | |
| 6,522,926 B1 | 2/2003 | Kieval et al. | |
| 6,575,994 B1 | 6/2003 | Marin et al. | |
| 6,616,624 B1 | 9/2003 | Kieval | |
| 6,622,041 B2 | 9/2003 | Terry et al. | |
| 6,632,991 B2 | 10/2003 | Chen | |
| 6,647,287 B1 | 11/2003 | Peel et al. | |
| 6,810,286 B2 | 10/2004 | Donovan et al. | |
| 6,824,561 B2 | 11/2004 | Soykan et al. | |
| 6,845,267 B2 | 1/2005 | Harrison et al. | |
| 6,850,801 B2 | 2/2005 | Kieval et al. | |
| 6,865,416 B2 | 3/2005 | Dev et al. | |
| 6,871,092 B2 | 3/2005 | Piccone | |
| 6,885,895 B1 | 4/2005 | Whitehurst et al. | |
| 6,939,345 B2 | 9/2005 | Ken Knight et al. | |
| 6,985,774 B2 | 1/2006 | Kieval et al. | |
| 7,044,981 B2 | 5/2006 | Liu et al. | |
| 7,090,648 B2 | 8/2006 | Sackner et al. | |
| 7,158,832 B2 | 1/2007 | Kieval et al. | |
| 7,167,751 B1 | 1/2007 | Whitehurst et al. | |
| 7,225,019 B2 | 5/2007 | Jahns et al. | |
| 7,292,886 B1 | 11/2007 | Kroll | |
| 7,299,091 B2 | 11/2007 | Barrett et al. | |
| 7,389,149 B2 | 6/2008 | Rossing et al. | |
| 7,395,119 B2 | 7/2008 | Hagen et al. | |
| 7,452,334 B2 | 11/2008 | Gianchandani et al. | |
| 7,476,200 B2 | 1/2009 | Tal | |
| 7,486,991 B2 | 2/2009 | Libbus et al. | |
| 7,623,926 B2 | 11/2009 | Rossing et al. | |
| 7,706,884 B2 | 4/2010 | Libbus | |
| 7,706,886 B2 | 4/2010 | Morimoto et al. | |
| 7,747,302 B2 | 6/2010 | Milledge et al. | |
| 7,765,000 B2 | 7/2010 | Zhang et al. | |
| 7,811,221 B2 | 10/2010 | Gross | |
| 8,249,705 B1 | 8/2012 | Kieval et al. | |
| 8,538,535 B2 | 9/2013 | Gross | |
| 8,626,290 B2 | 1/2014 | Dagan | |
| 8,626,299 B2 | 1/2014 | Gross | |
| 2001/0044434 A1 | 11/2001 | Lee et al. | |
| 2002/0016615 A1 * | 2/2002 | Dev et al. | 607/2 |
| 2002/0026228 A1 | 2/2002 | Schauerte | |
| 2002/0032468 A1 | 3/2002 | Hill et al. | |
| 2002/0077554 A1 | 6/2002 | Schwartz et al. | |
| 2002/0103454 A1 | 8/2002 | Sackner et al. | |
| 2003/0036773 A1 | 2/2003 | Whitehurst et al. | |
| 2003/0050683 A1 | 3/2003 | Boutos | |
| 2003/0055465 A1 | 3/2003 | Ben-Haim | |
| 2003/0055466 A1 | 3/2003 | Ben | |
| 2003/0055467 A1 | 3/2003 | Ben | |
| 2003/0060858 A1 | 3/2003 | Kieval et al. | |
| 2003/0130715 A1 | 7/2003 | Boutos | |
| 2003/0199806 A1 | 10/2003 | Kieval | |
| 2003/0204206 A1 | 10/2003 | Padua et al. | |
| 2004/0010303 A1 | 1/2004 | Bolea et al. | |
| 2004/0019364 A1 | 1/2004 | Kieval et al. | |
| 2004/0039417 A1 | 2/2004 | Soykan et al. | |
| 2004/0044393 A1 * | 3/2004 | Yarden et al. | 623/1.2 |
| 2004/0054384 A1 | 3/2004 | Nachum | |
| 2004/0106954 A1 | 6/2004 | Whitehurst et al. | |
| 2004/0106976 A1 | 6/2004 | Bailey et al. | |
| 2004/0133240 A1 | 7/2004 | Adams et al. | |
| 2004/0162590 A1 | 8/2004 | Whitehurst et al. | |
| 2004/0193092 A1 | 9/2004 | Deal | |
| 2004/0254616 A1 | 12/2004 | Rossing et al. | |
| 2005/0027346 A1 | 2/2005 | Arkusz et al. | |
| 2005/0033407 A1 | 2/2005 | Weber et al. | |
| 2005/0049680 A1 | 3/2005 | Fischell et al. | |
| 2005/0090867 A1 * | 4/2005 | Lapanashvili et al. | 607/3 |
| 2005/0096710 A1 | 5/2005 | Kieval | |
| 2005/0149130 A1 | 7/2005 | Libbus | |
| 2005/0149132 A1 | 7/2005 | Libbus | |
| 2005/0149155 A1 | 7/2005 | Scheiner et al. | |
| 2005/0154418 A1 | 7/2005 | Kieval et al. | |
| 2005/0203610 A1 | 9/2005 | Tzeng | |
| 2005/0209652 A1 | 9/2005 | Whitehurst et al. | |
| 2005/0232965 A1 | 10/2005 | Falotico | |
| 2005/0233962 A1 | 10/2005 | Lue et al. | |
| 2005/0240229 A1 | 10/2005 | Whitehurst et al. | |
| 2005/0251212 A1 | 11/2005 | Kieval et al. | |
| 2005/0288651 A1 | 12/2005 | VanTassel | |
| 2006/0004417 A1 | 1/2006 | Rossing et al. | |
| 2006/0004420 A1 | 1/2006 | Rossing et al. | |
| 2006/0004430 A1 | 1/2006 | Rossing et al. | |
| 2006/0074453 A1 | 4/2006 | Kieval et al. | |
| 2006/0100668 A1 | 5/2006 | Ben et al. | |
| 2006/0111626 A1 | 5/2006 | Rossing et al. | |
| 2006/0149124 A1 | 7/2006 | Forsell | |
| 2006/0149345 A1 | 7/2006 | Boggs et al. | |
| 2006/0167540 A1 | 7/2006 | Masters et al. | |
| 2006/0173507 A1 | 8/2006 | Mrva et al. | |
| 2006/0217588 A1 | 9/2006 | Gross et al. | |
| 2006/0259085 A1 | 11/2006 | Zhang et al. | |
| 2006/0265038 A1 | 11/2006 | Hagen et al. | |
| 2006/0293712 A1 | 12/2006 | Kieval et al. | |
| 2007/0021786 A1 | 1/2007 | Parnis et al. | |
| 2007/0021790 A1 | 1/2007 | Kieval et al. | |
| 2007/0021792 A1 | 1/2007 | Kieval et al. | |
| 2007/0021794 A1 | 1/2007 | Kieval et al. | |
| 2007/0021796 A1 | 1/2007 | Kieval et al. | |
| 2007/0021797 A1 | 1/2007 | Kieval et al. | |
| 2007/0021798 A1 | 1/2007 | Kieval et al. | |
| 2007/0021799 A1 | 1/2007 | Kieval et al. | |
| 2007/0027496 A1 | 2/2007 | Parnis et al. | |
| 2007/0038255 A1 | 2/2007 | Kieval et al. | |
| 2007/0038259 A1 | 2/2007 | Kieval et al. | |
| 2007/0038260 A1 | 2/2007 | Kieval et al. | |
| 2007/0038261 A1 | 2/2007 | Kieval et al. | |
| 2007/0038262 A1 | 2/2007 | Kieval et al. | |
| 2007/0049989 A1 | 3/2007 | Rossing et al. | |
| 2007/0060972 A1 | 3/2007 | Kieval et al. | |
| 2007/0100433 A1 | 5/2007 | Limon | |
| 2007/0106340 A1 | 5/2007 | Bolea et al. | |
| 2007/0142879 A1 | 6/2007 | Greenberg et al. | |
| 2007/0150009 A1 | 6/2007 | Kveen et al. | |
| 2007/0156179 A1 | 7/2007 | S.E. | |
| 2007/0156198 A1 | 7/2007 | Rossing et al. | |
| 2007/0156201 A1 | 7/2007 | Rossing | |
| 2007/0167984 A1 | 7/2007 | Kieval et al. | |
| 2007/0185540 A1 | 8/2007 | Ben | |
| 2007/0185542 A1 | 8/2007 | Bolea et al. | |
| 2007/0185543 A1 | 8/2007 | Rossing et al. | |
| 2007/0191904 A1 | 8/2007 | Libbus | |
| 2007/0248850 A1 | 10/2007 | Heller | |
| 2007/0276270 A1 | 11/2007 | Tran | |
| 2007/0276442 A1 | 11/2007 | Hagen et al. | |
| 2007/0276459 A1 | 11/2007 | Rossing et al. | |
| 2007/0282385 A1 | 12/2007 | Rossing et al. | |
| 2007/0293927 A1 | 12/2007 | Frank et al. | |

(56) References Cited

U.S. PATENT DOCUMENTS

| | | |
|---|---|---|
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0046054 A1 | 2/2008 | Hjelle et al. |
| 2008/0051767 A1 | 2/2008 | Rossing et al. |
| 2008/0051849 A1 | 2/2008 | Ben-Haim |
| 2008/0058889 A1 | 3/2008 | Ben-Haim |
| 2008/0058891 A1 | 3/2008 | Ben-Haim |
| 2008/0071363 A1 | 3/2008 | Tuval et al. |
| 2008/0082137 A1 | 4/2008 | Kieval et al. |
| 2008/0097540 A1 | 4/2008 | Bolea et al. |
| 2008/0119898 A1 | 5/2008 | Ben-David et al. |
| 2008/0119911 A1 | 5/2008 | Rosero |
| 2008/0132972 A1 | 6/2008 | Shuros et al. |
| 2008/0140167 A1 | 6/2008 | Hagen et al. |
| 2008/0154349 A1 | 6/2008 | Rossing et al. |
| 2008/0161865 A1 | 7/2008 | Hagen |
| 2008/0161887 A1 | 7/2008 | Hagen |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177364 A1 | 7/2008 | Bolea et al. |
| 2008/0195174 A1 | 8/2008 | Walker et al. |
| 2008/0215117 A1 | 9/2008 | Gross |
| 2009/0005859 A1 | 1/2009 | Keilman |
| 2009/0036975 A1 | 2/2009 | Ward et al. |
| 2009/0112285 A1 | 4/2009 | Cahan |
| 2009/0198308 A1 | 8/2009 | Gross et al. |
| 2009/0204170 A1 | 8/2009 | Hastings et al. |
| 2009/0228078 A1 | 9/2009 | Zhang et al. |
| 2010/0010556 A1 | 1/2010 | Zhao et al. |
| 2010/0042186 A1 | 2/2010 | Ben-David et al. |
| 2010/0076247 A1 | 3/2010 | Zilbershlag et al. |
| 2010/0094373 A1 | 4/2010 | Sharma |
| 2010/0211131 A1 | 8/2010 | Williams et al. |
| 2010/0305392 A1 | 12/2010 | Gross et al. |
| 2011/0118773 A1 | 5/2011 | Gross |
| 2011/0137370 A1 | 6/2011 | Gross |
| 2012/0035679 A1 | 2/2012 | Dagan |
| 2012/0035711 A1 | 2/2012 | Gross |
| 2012/0158081 A1 | 6/2012 | Gross |
| 2013/0123880 A1 | 5/2013 | Dagan |
| 2013/0338748 A1 | 12/2013 | Dagan |

FOREIGN PATENT DOCUMENTS

| | | |
|---|---|---|
| WO | 8401905 | 5/1984 |
| WO | WO9926530 A1 | 6/1999 |
| WO | WO-0226314 | 4/2002 |
| WO | WO-03076008 | 9/2003 |
| WO | WO-03082080 | 10/2003 |
| WO | WO-03082403 | 10/2003 |
| WO | WO-2004073484 | 9/2004 |
| WO | WO-2005084389 | 9/2005 |
| WO | WO-2005097256 | 10/2005 |
| WO | WO-2006012033 | 2/2006 |
| WO | WO-2006012050 | 2/2006 |
| WO | WO-2006032902 | 3/2006 |
| WO | WO-2006041664 | 4/2006 |
| WO | 2006/098928 | 9/2006 |
| WO | WO-2006125163 | 11/2006 |
| WO | WO-2007013065 | 2/2007 |
| WO | WO-2007047152 | 4/2007 |
| WO | WO-2007114860 | 10/2007 |
| WO | WO-2007118090 | 10/2007 |
| WO | WO-2007136850 | 11/2007 |
| WO | WO-2007136851 | 11/2007 |
| WO | WO-2008039982 | 4/2008 |
| WO | WO-2008083120 | 7/2008 |
| WO | WO-2008083235 | 7/2008 |
| WO | 2009/017647 | 2/2009 |
| WO | 2009/095920 A2 | 8/2009 |
| WO | 2012/017437 A1 | 2/2012 |
| WO | 2012/085907 A2 | 6/2012 |
| WO | 2013/035092 A2 | 3/2013 |
| WO | 2013/069020 A1 | 5/2013 |
| WO | 2013/164829 A1 | 11/2013 |

OTHER PUBLICATIONS

An International Search Report and a Written Opinion both dated Dec. 19, 2011, which issued during the prosecution of Applicant's PCT/IL11/00636.

An Office Action dated Mar. 13, 2012, which issued during the prosecution of U.S. Appl. No. 12/023,896.

Levenberg, S. "Endothelial Cells Derived from Human Embryonic Stem Cells." Proceedings of the National Academy of Sciences USA. vol. 99, No. 7, p. 4391-4396 (2002).

Taylor et al., "The unequal influences of the left and right vagi on the control of the heart and pulmonary artery in the rattlesnake, *Crotalus durissus*", The Journal of Experimental Biology 212:145-151 (2008).

Hamilton and Feigl, "Coronary vascular sympathetic beta-receptor innervation", American Journal of Physiology, 230 (6):1569-1576 (1976).

Office Action for U.S. Appl. No. 12/023,896 dated Aug. 9, 2011.

International Search Report dated Jan. 24, 2007, issued for Application No. PCT/IL2006/000856.

International Preliminary Report on Patentability dated Jan. 29, 2008, issued for Application No. PCT/IL2006/000856.

U.S. Appl. No. 60/721,728, filed Sep. 28, 2005.

U.S. Appl. No. 60/702,491, filed Jul. 25, 2005.

An Office Action dated Mar. 15, 2012, which issued during the prosecution of U.S. Appl. No. 12/792,227.

An International Search Report and a Written Opinion both dated Jul. 5, 2012, which issued during the prosecution of Applicant's PCT/IL11/00952.

An Office Action dated Aug. 1, 2012, which issued during the prosecution of U.S. Appl. No. 12/957,799.

An Office Action dated Aug. 29, 2012, which issued during the prosecution of U.S. Appl. No. 12/792,227.

An Office Action dated Jul. 18, 2012, which issued during the prosecution of U.S. Appl. No. 13/210,778.

An International Search Report and a Written Opinion both dated Aug. 8, 2013, which issued during the prosecution of Applicant's PCT/IL2013/050375.

An Office Action dated Dec. 13, 2013, which issued during the prosecution of U.S. Appl. No. 13/294,062, 9 pages.

An Office Action dated Jan. 27, 2014, which issued during the prosecution of U.S. Appl. No. 12/023,896, 11 pages.

Extended European Search Report dated Oct. 31, 2013 which issued during the prosecution of Applicant's European App No. 11814203. 3, 7 pages.

An Office Action dated Dec. 20, 2013, which issued during the prosecution of U.S. Appl. No. 12/792,227, 10 pages.

* cited by examiner

ELECTRICAL STIMULATION OF BLOOD VESSELS

CROSS-REFERENCES TO RELATED APPLICATIONS

The present application is a U.S. national phase of PCT Application No. PCT/IL06/000856 to Gross et al. (published as WO 07/013,065), filed Jul. 25, 2006, which claims the benefit of: (a) U.S. Provisional Application 60/702,491, filed Jul. 25, 2005, entitled, "Electrical stimulation of blood vessels," and (b) U.S. Provisional Application 60/721,728, filed Sep. 28, 2005, entitled, "Electrical stimulation of blood vessels," both of which applications are incorporated herein by reference.

FIELD OF THE INVENTION

The present invention relates generally to implantable medical devices, and specifically to methods and apparatus for stimulating and replacing blood vessels.

BACKGROUND OF THE INVENTION

U.S. Pat. Nos. 6,865,416 and 6,347,247 to Dev et al., which are incorporated herein by reference, describe methods for inducing or increasing the vasodilation of a vessel, or the flow of blood therethrough, including applying an electrical impulse to the vessel. According to the inventors in the '416 and 247 applications, the induction or increase of vessel vasodilation by an electrical impulse appears to result either from a direct effect caused by the electrical current applied to the vessel, or an indirect effect resulting from the release or stimulation of factors that promote vasodilation, such as the release of endothelium derived relaxation factors (EDRF) currently identified as nitric oxide (NO) or other vasodilating substances triggered by the electrical pulses applied to the cells of the vessel. In an embodiment, a double-balloon catheter system incorporating electroporation technology is used to apply the electrical impulse endoluminally.

US Patent Application Publication 2003/0204206 to Padua et al., which is incorporated herein by reference, describes techniques for regulating delivery of therapeutic proteins and nucleic acids. The techniques include using a genetically-engineered electrically-responsive promoter operably linked to a therapeutic gene sequence, wherein expression of said sequence is controlled by an electrical pulse generator. In an embodiment, the pulse generator is able to deliver charge balanced electrical pulses at rate of about 10 to 100 Hz, preferably about 30 to 80 Hz, and more preferably about 50 to 60 Hz. In an embodiment, an implantable system uses an RF signal to communicate and generate an electrical current in a coiled stent. In an embodiment, an electric field is applied to engineered cells grown on a scaffolding, using either a conductive matrix having parallel electrodes, or a conductive stent matrix.

U.S. Pat. No. 6,845,267 to Harrison et al., which is incorporated herein by reference, describes an implantable control unit adapted to apply stimulating drugs and/or electrical pulses to predetermined areas affecting circulatory perfusion. In an embodiment, the implantable control unit applies electrical stimulation directly to smooth muscle to modulate its contractile state. The '267 patent states that relatively low frequency electrical stimulation ([sic] than about 50-100 Hz) tends to excite smooth muscle and lead to contraction, and relatively high frequency electrical stimulation tends to relax smooth muscle and lead to dilation. In an embodiment, electrical and/or drug stimulation is applied to autonomic sites responsible for innervation of the coronary arteries, and/or directly to the smooth muscle surrounding these arteries, in order to dilate the coronary arteries and provide relief from cardiac ischemia. For some applications, the implantable control unit includes an electrical coil or other means of receiving energy and/or information inside the package, which receives power and/or data by inductive or radio-frequency (RF) coupling to a transmitting coil placed outside the body. For some applications, the control unit communicates with other implanted stimulators, other implanted devices, and/or devices external to a patient's body, e.g., via an RF link, an ultrasonic link, or an optical link.

U.S. Pat. No. 6,871,092 to Piccone, which is incorporated herein by reference, describes apparatus for the treatment of vascular, muscle and/or tendon disorders, for increasing the production of Vascular Endothelial Growth Factor (VEGF), for anti-inflammatory treatment, and/or for the activation of microcirculation. The apparatus generates and applies electrical pulses through the epidermis of a subject. The pulses are described as inducing a biochemical response which not only eliminates inflammation from the part of the body treated and reduces or eliminates pain, but also has a rapid muscle-relaxant effect, and stimulates vasodilatation and VEGF production.

US Patent Application Publication 2004/0106954 to Whitehurst et al., which is incorporated herein by reference, describes techniques for treating congestive heart failure (CHF) by implanting of a discharge portion of a catheter and, optionally, an electrode on a lead, near tissue to be stimulated. Stimulation pulses, such as drug infusion pulses and optional electrical pulses, are supplied by a stimulator implanted remotely, and through the catheter or lead, which is tunneled subcutaneously between the stimulator and stimulation site. Stimulation sites include the coronary arteries, the aorta, the left ventricle, the left atrium, and/or the pulmonary veins, among other locations. For some applications, a stimulator includes electrical circuitry (including, for example, an inductive coil) for receiving data and/or power from outside the body by inductive, radio frequency (RF), or other electromagnetic coupling. For some applications, the stimulator communicates with other implanted stimulators, other implanted devices, and/or devices external to a patient's body via, e.g., an RF link, an ultrasonic link, a thermal link, and/or an optical link.

US Patent Application Publication 2006/0074453 to Kieval et al., which is incorporated herein by reference, describes a method for treating heart failure in a patient, including activating a baroreflex system of the patient with at least one baroreflex activation device and resynchronizing the patient's heart with a cardiac resynchronization device. Activating the baroreflex system and resynchronizing the heart may be performed simultaneously or sequentially, in various embodiments. A device for treating heart failure includes a baroreflex activation member coupled with a cardiac resynchronization member. The baroreflex activation member may comprise a wide variety of devices which utilize mechanical, electrical, thermal, chemical, biological, or other means to activate baroreceptors and/or other tissues. In many embodiments, particularly the mechanical activation embodiments, the baroreflex device indirectly activates one or more baroreceptors by stretching or otherwise deforming the vascular wall surrounding the baroreceptors.

US Patent Application Publication 2003/0060858 to Kieval et al., which is incorporated herein by reference, describes techniques for selectively and controllably reducing blood pressure, nervous system activity, and neurohormonal activity by activating baroreceptors. A baroreceptor activation device is positioned near a baroreceptor, for example a baroreceptor in the carotid sinus. A control system may be used to modulate the baroreceptor activation device. In some embodiments, the baroreceptor activation device takes the form of an intravascular deformable structure. The deformable structure device includes a coil, braid or other stent-like structure disposed in the vascular lumen. In other embodiments, the baroreceptor activation device takes the form of an extravascular deformable structure, which is disposed about the vascular wall, and therefore compresses, rather than expands, the vascular wall. The deformable structure device includes a coil, braid or other stent-like structure.

U.S. Pat. No. 6,086,527 to Talpade, which is incorporated herein by reference, describes a system for regulating blood flow to a portion of the vasculature, such as the renal system, in order to treat heart disease. A regulator maintains blood flow so as to control physiological feedback responses in order to relieve overload conditions on the heart.

US Patent Application Publication 2002/0103454 to Sackner et al., which is incorporated herein by reference, describes methods of medical treatment and diagnosis using mediators released by endothelial cells stimulated by external addition of pulses to the circulation. The external pulses produce circumferential shear stress in body fluid channels that subsequently stimulates the endothelial cells to produce mediators that become available for therapeutic and diagnostic purposes. The preferred means of adding external pulses is the mechanical inducement of periodic acceleration of the body or parts of the body by a reciprocating motion platform.

US Patent Application Publication 2005/0149130 to Libbus et al., which is incorporated herein by reference, describes a baroreflex stimulator including a pulse generator for providing a baroreflex stimulation signal through an electrode, and a modulator to modulate the baroreflex stimulation signal based on a circadian rhythm template. In some embodiments, the stimulator includes a sensor to sense automatic nervous system (ANS) activity. Such a sensor can be used to perform feedback in a closed loop control system. For example, various embodiments sense surrogate parameters, such as respiration and blood pressure, indicative of ANS activity.

The following patents and patent application publications, all of which are incorporated herein by reference, may be of interest:

U.S. Pat. No. 6,824,561 and US Patent Application Publication 2004/0039417 to Soykan et al.

U.S. Pat. No. 6,810,286 to Donovan et al.

U.S. Pat. No. 6,463,323 to Conrad-Vlasak et al.

U.S. Pat. No. 6,058,331 to King

U.S. Pat. No. 6,200,259 to March

US Patent Application Publication 2003/0036773 to Whitehurst et al.

European Patent Application Publication EP 0 109 935 A1 to Charmillot et al.

Levenberg S et al., in an articled entitled, "Endothelial cells derived from human embryonic stem cells," Proc Natl Acad Sci USA 99(7):4391-6 (2002) Epub 2002 Mar. 26, which is incorporated herein by reference, describe the differentiation steps of human embryonic stem cells into endothelial cells forming vascular-like structures.

SUMMARY OF THE INVENTION

In some embodiments of the present invention, an electrode device is adapted to be inserted into a blood vessel. The electrode device comprises one or more electrodes that are adapted to apply an electrical signal to a wall of the blood vessel, and to configure the signal to induce an increase in nitric oxide (NO) secretion by the wall.

For some applications, stimulation using the electrode device causes healing of the blood vessel. For example, the stimulation may (a) reduce a level of atherosclerosis of the blood vessel, (b) have an anti-inflammatory and/or antithrombotic effect on the blood vessel, (c) increase endothelial cell growth, (d) reduce smooth muscle cell growth (e.g., to reduce blockage of the blood vessel), and/or (e) reduce plaque activity. For applications in which the blood vessel includes a coronary artery, stimulation using the electrode device typically dilates the coronary artery, thereby treating cardiac ischemia.

In some embodiments of the present invention, the electrode device is adapted to apply the signal to an artificial blood vessel graft that has been implanted in the subject. Endothelial cells often grow into the lumen of such grafts. This growth is generally viewed as desirable. However, such growth sometimes causes platelets to accumulate in and thereby block the lumen. The signal applied by the electrode device is configured to induce an increase in NO secretion by the endothelial cells in the lumen, which increased NO secretion de-aggregates the platelets. Alternatively or additionally, the signal applied by the electrode device is configured to stimulate cell growth in the lumen of the artificial graft.

For some applications, the electrode device comprises at least one stent. The electrodes are coupled to the stent, or are integrated into structural elements of the stent. For some applications, the stent comprises a bifurcation stent. The electrode device is configured to induce an increase in NO secretion by a wall of the blood vessel, typically in order to reduce platelet aggregation outside the stent (such as between the stent and the wall) and/or to minimize restenosis.

In some embodiments of the present invention, the electrode device is used to apply electrical stimulation during the process of deriving blood vessels (i.e., veins or arteries) from stem cells, such as from embryonic stem cells. Alternatively or additionally, the electrode device is used to apply electrical stimulation to blood vessels derived from stem cells after the blood vessels have been implanted in a subject. Further alternatively or additionally, the electrode device is used to apply electrical stimulation to tissue-based blood vessels created by another technique. An increase in NO production caused by such stimulation may be beneficial for the blood vessels, e.g., may aid the process of differentiating the stem cells into the blood vessels.

In some embodiments of the present invention, a counterpulsation device is adapted to be inserted in an ascending aorta and/or a descending aorta of a subject. The counterpulsation device comprises one or more electrodes, and an implantable or external control unit. The control unit is adapted to drive the electrodes to apply an electrical signal to a wall of the aorta during systole, and to configure the signal to induce an increase in NO secretion by the wall. The increased NO secretion dilates the wall such that during systole the wall stores energy, and pressure on the heart is reduced. During diastole, the wall constricts, releasing the stored energy and thereby increasing blood pressure and coronary blood flow. For some applications, the control unit is additionally configured to drive the electrodes to apply, during diastole, stimulation configured to enhance the rapid constriction of the aorta.

In some embodiments of the present invention, an artificial artery is provided that is configured to assume a first cross-sectional shape during a first phase of a cardiac cycle (e.g., systole or diastole), and a second cross-sectional shape during a second phase of the cardiac cycle (e.g., diastole or systole). Typically, both of the cross-sectional shapes are elliptical, and have major axes with different lengths. For some applications, one of the cross-sectional shapes is substantially circular (i.e., the major and minor axes are substantially the same). Such shape changing during each cardiac cycle generally reduces the likelihood of the artificial artery becoming blocked over time.

In an embodiment of the present invention, one or more electrodes are placed in or adjacent to an eye of a subject, and are driven to apply a signal that induces NO production adjacent to the electrodes, in order to treat an eye disease. For example, the increased NO production may be used to reduce intraocular pressure, in order to treat glaucoma. Alternatively or additionally, increased blood flow induced by arterial dilation cause by the NO production minimizes optic nerve degeneration, such as is seen in age-related macular degeneration (AMD). Alternatively or additionally, the increased blood flow in one or more retinal arteries treats or prevents diabetic retinopathy.

There is therefore provided, in accordance with an embodiment of the present invention, apparatus including:

a bifurcation stent including one or more electrodes, the stent configured to be placed in a primary passage and a secondary passage of a blood vessel; and a control unit, configured to drive the electrodes to apply a signal to a wall of the blood vessel, and to configure the signal to increase nitric oxide (NO) secretion by the wall.

For some applications, the control unit is adapted to configure the signal to reduce platelet aggregation outside the stent between the stent and the wall of the blood vessel.

For some applications, the control unit is configured to drive the electrodes to apply the signal with a frequency of between 3 and 20 Hz, and/or a voltage of less than 5 volts.

There is further provided, in accordance with an embodiment of the present invention, apparatus for applying counterpulsation to an aorta of a subject, the apparatus including:

one or more electrodes, adapted to be inserted into the aorta; and a control unit, configured to:

drive the electrodes to apply a systolic electrical signal to a wall of the aorta during at least a portion of systole, configure the systolic signal to induce an increase in nitric oxide (NO) secretion by the wall, and withhold driving the electrodes to apply the systolic signal to the wall during at least a portion of diastole.

In an embodiment, the apparatus includes a physiological sensor, which is configured to generate a sensor signal, and the control unit is configured to set at least one parameter of the systolic signal responsively to the sensor signal.

For some applications, the control unit is configured to drive the electrodes to begin application of the systolic signal slightly prior to a commencement of systole. For some applications, the control unit is configured to drive the electrodes to begin application of the systolic signal less than 50 ms prior to a commencement of systole.

For some applications, the control unit is adapted to configure the systolic signal to have an amplitude of between 1 and 10 mA, and/or a frequency of less than 30 Hz.

In an embodiment, the control unit is adapted to drive the electrodes to apply a diastolic electrical signal to the wall during at least a portion of diastole, and to configure the diastolic signal to enhance constriction of the aorta during diastole. For some applications, the control unit is adapted to configure a diastolic value of a parameter of the diastolic signal to be between 1.5 and 4 times a systolic value of the parameter of the systolic signal, the parameter selected from the group consisting of: an amplitude, and a frequency. For some applications, the control unit is adapted to configure the diastolic signal to have an amplitude of between 5 and 20 mA, and/or a frequency of between 15 and 100 Hz.

In an embodiment, the apparatus includes an element configured to mechanically dilate the aorta during at least a portion of systole. For some applications, the element is configured to be placed at least partially in the aorta. Alternatively or additionally, the element is configured to be placed at least partially outside the aorta. For some applications, the element is configured to serve as at least one of the one or more electrodes.

There is still further provided, in accordance with an embodiment of the present invention, apparatus including an artificial artery configured to assume a first cross-sectional shape during a first phase of a cardiac cycle, and a second cross-sectional shape during a second phase of the cardiac cycle.

For some applications, exactly one of the first and second cross-sectional shapes is substantially circular.

For some applications, the first and second phases include systole and diastole, respectively, and the artificial artery is configured to assume the first and second cross-sectional shapes during systole and diastole, respectively.

In an embodiment, the first and second cross-sectional shapes are elliptical, having respective major axes having first and second lengths, respectively. For some applications, a ratio of the first length to the second length is at least 1.1, such as at least 1.3.

There is additionally provided, in accordance with an embodiment of the present invention, apparatus for treating an eye of a subject, the apparatus including:

one or more electrodes, configured to be placed at least partially in the eye; and a control unit, configured to treat the eye by driving the electrodes to apply an electrical signal to the eye that induces production of nitric oxide (NO).

In an embodiment, the control unit is configured to drive the electrodes to apply the signal to induce the NO production sufficiently to induce dilation of a retinal artery of the subject.

In an embodiment, the control unit is configured to drive the electrodes to apply the signal to induce the NO production sufficiently to minimize degeneration of an optic nerve of the subject.

For some applications, the control unit is configured to be placed in the eye, and the apparatus includes a photovoltaic cell that is configured to power the control unit. For some applications, at least one of the electrodes includes a coil that is configured to receive energy inductively from the control unit. For some applications, at least one of the electrodes is configured to be placed at a site posterior to a retina of the eye.

In an embodiment, the control unit is configured to drive the electrodes to apply the signal to induce the NO production sufficiently to reduce an intraocular pressure of the eye. For some applications, the electrodes are configured to be placed around a cornea of the eye, and the control unit is configured to drive the electrodes to apply the signal to induce the NO production in a vicinity of a trabecular meshwork of the eye.

There is still additionally provided, in accordance with an embodiment of the present invention, apparatus for application to a blood vessel of a subject, the apparatus including:

one or more electrodes, configured to be placed in or outside the blood vessel in a vicinity of a baroreceptor of the subject, such that the electrodes are in electrical communication with the blood vessel; and a control unit, configured to drive the electrodes to apply an electrical signal to the blood vessel, and to configure the signal to induce an increase in nitric oxide (NO) secretion by a wall of the blood vessel sufficiently to cause dilation of the wall, thereby activating the baroreceptor.

In an embodiment, the apparatus includes an element configured to mechanically dilate the blood vessel in the vicinity of the baroreceptor. In an embodiment, the electrodes are configured to apply mechanical force to the wall that is sufficient to change a shape of the wall.

In an embodiment, the apparatus includes a sensor configured to sense a feature of a cardiac cycle of the subject and to output a sensor signal responsively thereto, and the control unit is configured to drive the electrodes to apply the signal responsively to the sensor signal. For some applications, the control unit is configured to apply the signal during at least a portion of systole, and to withhold applying the signal during at least a portion of diastole.

In an embodiment, the electrodes are configured to be placed in the blood vessel, and are shaped so as to define springy rib-shaped elements. For some applications, the apparatus includes one or more piezoelectric elements positioned in direct or indirect mechanical contact with the rib-shaped elements, and the apparatus is configured such that pulsing of the blood vessel causes the piezoelectric elements to generate power, and the control unit is configured to use the power to drive the electrodes to apply the signal.

There is also provided, in accordance with an embodiment of the present invention, a method including:
placing a bifurcation stent including one or more electrodes in a primary passage and a secondary passage of a blood vessel;
driving the electrodes to apply a signal to a wall of the blood vessel; and
configuring the signal to increase nitric oxide (NO) secretion by the wall.

There is further provided, in accordance with an embodiment of the present invention, a method for applying counterpulsation to an aorta of a subject, the method including:
applying a systolic electrical signal to a wall of the aorta during at least a portion of systole;
configuring the systolic signal to induce an increase in nitric oxide (NO) secretion by the wall; and
withholding applying the systolic signal to the wall during at least a portion of diastole.

There is still further provided, in accordance with an embodiment of the present invention, a method including:
providing an artificial artery configured to assume a first cross-sectional shape during a first phase of a cardiac cycle, and a second cross-sectional shape during a second phase of the cardiac cycle; and
grafting the artificial artery to a natural artery of the subject.

In an embodiment, grafting includes grafting during a coronary bypass procedure.

There is additionally provided, in accordance with an embodiment of the present invention, a method for treating a subject, including:
identifying that the subject suffers from a condition of an eye; and
treating the eye condition by inducing production of nitric oxide (NO) in the eye by applying an electrical signal to the eye.

In an embodiment, identifying includes identifying that the subject suffers from glaucoma, and applying the signal includes configuring the signal to induce the NO production sufficiently to reduce an intraocular pressure of the eye. For some applications, applying the signal includes applying the signal around a cornea of the eye to induce the NO production in a vicinity of a trabecular meshwork of the eye.

There is also provided, in accordance with an embodiment of the present invention, a method including:
applying an electrical signal to a blood vessel of a subject in a vicinity of a baroreceptor of the subject; and
activating the baroreceptor by configuring the signal to induce an increase in nitric oxide (NO) secretion by a wall of the blood vessel sufficiently to cause dilation of the wall.

There is further provided, in accordance with an embodiment of the present invention, a method including:
implanting an artificial blood vessel in a subject;
applying an electrical signal to the artificial blood vessel; and
configuring the signal to induce an increase in nitric oxide (NO) secretion by endothelial cells that grow in a lumen of the artificial blood vessel.

In an embodiment, configuring the signal includes configuring the signal to induce the NO secretion to de-aggregate platelets accumulated as a result of growth of the endothelial cells. In an embodiment, configuring the signal includes configuring the signal to induce growth of the endothelial cells in the lumen. In an embodiment, configuring the signal includes configuring the signal to have a frequency of between 3 and 20 Hz.

For some applications, configuring the signal includes configuring the signal to have a voltage of less than 5 volts.

There is still further provided, in accordance with an embodiment of the present invention, a method for deriving a blood vessel from stem cells, including:
inducing the stem cells to differentiate into the blood vessel;
applying an electrical signal to at least one cell selected from the group consisting of: one of the stem cells, a cell of the blood vessel as the blood vessel is being derived, and a cell of the blood vessel after the blood vessel has been derived; and
configuring the signal to induce an increase in nitric oxide (NO) secretion by the selected at least one cell.

In an embodiment, the at least one cell includes at the one of the stem cells, and applying the signal includes applying the signal to the one of the stem cells. In an embodiment, the at least one cell includes the cell of the blood vessel as the blood vessel is being derived, and applying the signal includes applying the signal to the cell of the blood vessel as the blood vessel is being derived. In an embodiment, the at least one cell includes the cell of the blood vessel after the blood vessel has been derived, and applying the signal includes applying the signal to the cell of the blood vessel after the blood vessel has been derived.

There is additionally provided, in accordance with an embodiment of the present invention, a method including:
identifying buildup of plaque on a wall of a blood vessel of a subject as being in a vicinity of a baroreceptor of the subject; and
increasing flexibility of the artery in the vicinity by removing the plaque from the artery.

In an embodiment, the blood vessel is selected from the group consisting of: a carotid artery, and an aorta in a vicinity of an aortic arch.

The present invention will be more fully understood from the following detailed description of embodiments thereof, taken together with the drawings, in which:

DETAILED DESCRIPTION OF EMBODIMENTS

Figure 1:
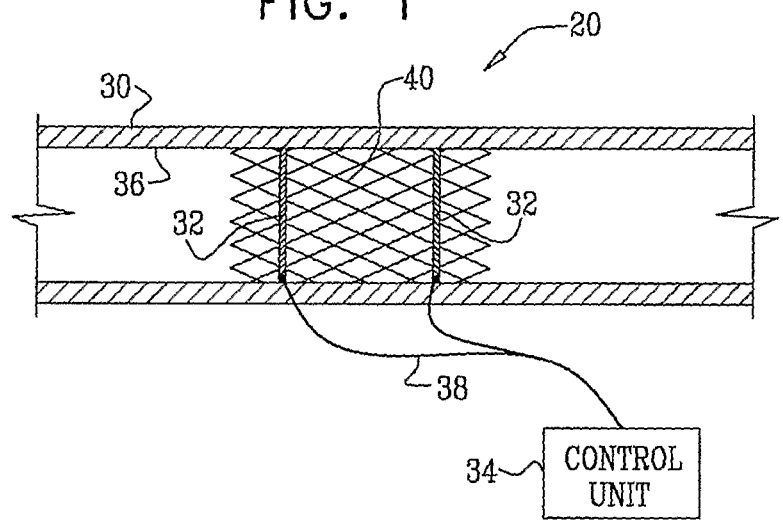
FIG. 1 is a schematic illustration of an electrode device adapted to be inserted into a blood vessel of a subject, in accordance with an embodiment of the present invention.

FIG. 1 is a schematic illustration of an electrode device 20 adapted to be inserted into a blood vessel 30 of a subject, in accordance with an embodiment of the present invention. Electrode device 20 comprises one or more electrodes 32, and an implantable or external control unit 34. Control unit 34 is adapted to drive electrodes 32 to apply an electrical signal to a wall 36 of blood vessel 30, and to configure the signal to induce an increase in nitric oxide (NO) secretion by wall 36. For some applications, wall 36 secretes the NO into the lumen of blood vessel 30. Alternatively or additionally, wall 36 secretes the NO into tissue of the blood vessel. For some applications, blood vessel 30 includes an atherosclerotic blood vessel. For some applications, blood vessel 30 includes a coronary artery, a bypass graft (such as a coronary artery bypass graft (CABG)), a retinal artery, a pancreatic artery, or a penile artery (e.g., to treat erectile dysfunction). The applied signal treats erectile dysfunction by functioning as a pump to enhance blood flow (e.g., for a diabetic patient), and/or by generating NO as a signaling molecule which enhances erection.

For some applications, stimulation using electrode device 20 causes healing of blood vessel 30. For example, the stimulation may (a) reduce a level of atherosclerosis of the blood vessel, (b) have an anti-inflammatory and/or antithrombotic effect on the blood vessel, (c) increase endothelial cell growth, (d) reduce smooth muscle cell growth (e.g., to reduce blockage of blood vessel 30), and/or (e) reduce plaque activity. For some applications, electrode device 20 is configured to drive electrodes 32 to apply the signal for a period of at least one week, such as at least one month, or at least several months. Such long-term stimulation may contribute to healing of the blood vessel. For applications in which blood vessel 30 includes a coronary artery, stimulation using electrode device 20 typically dilates the coronary artery, thereby treating cardiac ischemia.

In an embodiment of the present invention, electrode device 20 is adapted to apply the signal to an artificial blood vessel graft that has been implanted in the subject. Endothelial cells often grow into the lumen of such grafts. This growth is generally viewed as desirable. However, such growth sometimes causes platelets to accumulate in and thereby block the lumen. The signal applied by electrode device 20 is configured to induce an increase in NO secretion by the endothelial cells in the lumen, which increased NO secretion de-aggregates the platelets. Alternatively or additionally, the signal applied by electrode device 20 is configured to stimulate cell growth in the lumen of the artificial graft. These stimulation techniques may be used, for example, with synthetic vascular grafts manufactured by W. L. Gore & Associates (Newark, Del., USA).

In an embodiment of the present invention, electrode device 20 comprises at least one stent 40. For some applications, electrodes 32 are coupled to stent 40, as shown in FIG. 1. Alternatively or additionally, structural elements of stent 40 additionally serve as one or more of electrodes 32. For some applications, electrodes 32 comprise ring electrodes, as shown in FIG. 1. For some applications, electrodes 32 comprise elongated cylinders, through which blood can flow (configuration not shown). In an embodiment, electrodes 32 are not hollow, and blood does not pass through them. Instead, for example, the electrodes may effectively be point electrodes, or be shaped as needle electrodes that slightly penetrate tissue adjacent thereto. It is thus to be seen that various shapes may be appropriate for electrodes 32, depending on each particular application.

Figure 2:
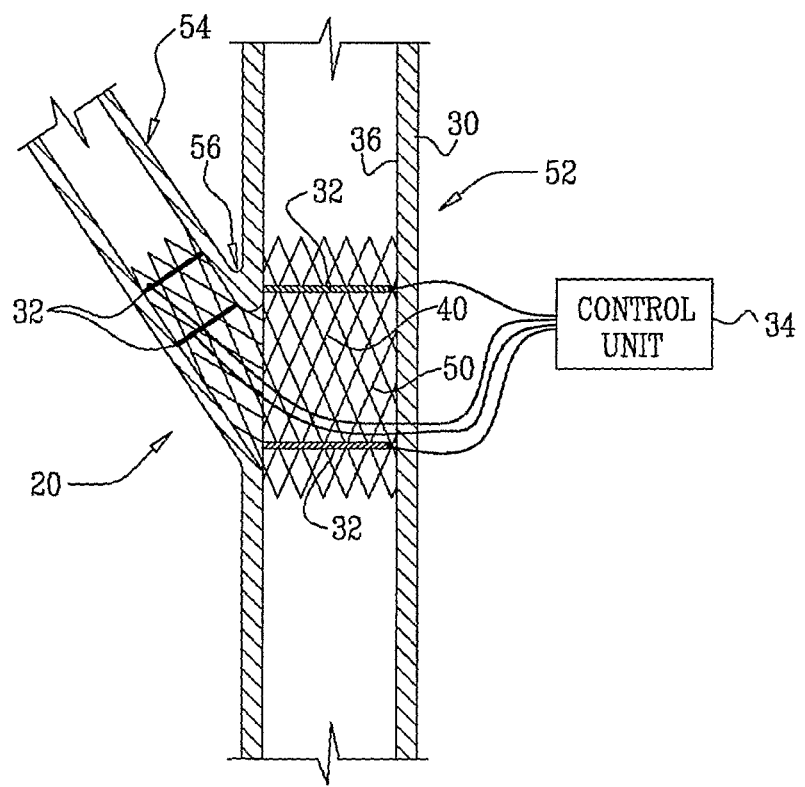
FIG. 2 is a schematic illustration of the electrode device of FIG. 1 comprising a bifurcation stent, in accordance with an embodiment of the present invention.

Reference is made to FIG. 2, in which stent 40 is shown comprising a bifurcation stent 50, in accordance with an embodiment of the present invention. Control unit 34 is adapted to induce an increase in NO secretion by wall 36 of blood vessel 30, typically in order to reduce platelet aggregation outside the stent, such as between the stent and wall 36. For some applications, electrode device 20 comprises two or more stents 40, at least a first one of which is adapted to be placed in a primary passage 52 of blood vessel 30, and at least a second one of which is adapted to be placed in a secondary passage 54 of blood vessel 30 in a vicinity of a bifurcation 56.

The particular lattice configuration of stent 40 shown in FIGS. 1 and 2 is for illustrative purposes only. Stent 40 may comprise other configurations known in the art. For some applications, stent 40 comprises two elements arranged in a double helix (configuration not shown). Typically, one of the elements serves as an anode and the other as a cathode of electrodes 32.

Figure 3:
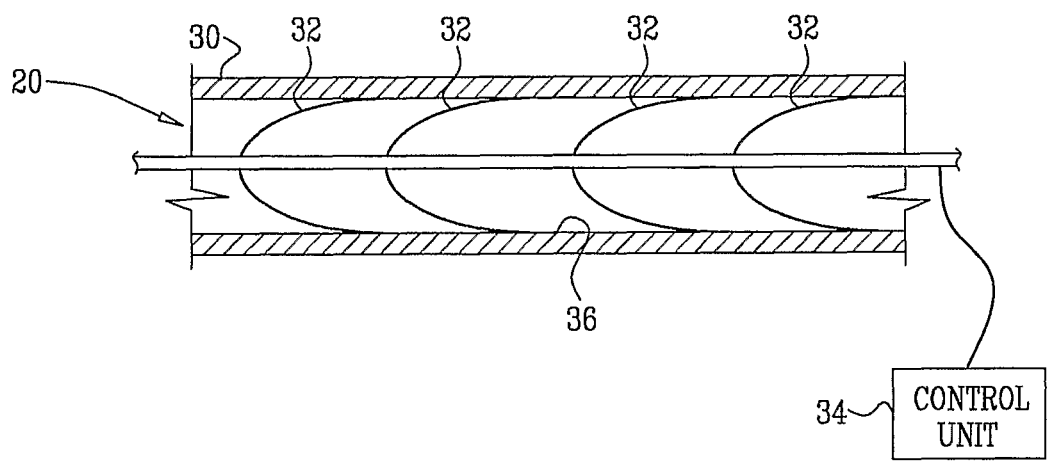
FIG. 3 is a schematic illustration of another configuration of the electrode device of FIG. 1, in accordance with an embodiment of the present invention.

FIG. 3 is a schematic illustration of another configuration of electrode device 20, in accordance with an embodiment of the present invention. In this embodiment, electrodes 32 are springy, and are configured to expand into contact with wall 36 of blood vessel 30. For example, the electrodes may be shaped so as define springy rib-shaped elements. For some applications, electrodes 32 are configured to apply a sufficient mechanical force to wall 36 to change a shape of the wall. For some applications, electrode device 20 is configured to be placed in a vicinity of a baroreceptor, and to both apply an electrical signal to the baroreceptor and change the shape of wall 36 in the vicinity of the baroreceptor. For some applications, the springiness of ribs of the electrodes is adjustable, such as by mechanical, electrical, or thermal means (e.g., at least a portion of the electrodes may comprises nitinol). The springiness may be mechanically adjusted by sliding a portion of the ribs into a chamber such that such portion is no longer springy.

For some applications, electrode device 20 comprises one or more piezoelectric elements positioned in direct or indirect mechanical contact with the ribs of the electrodes. Pulsing of blood vessel 30 causes the piezoelectric elements to generate sufficient power for applying the electrical signal.

Figure 4:
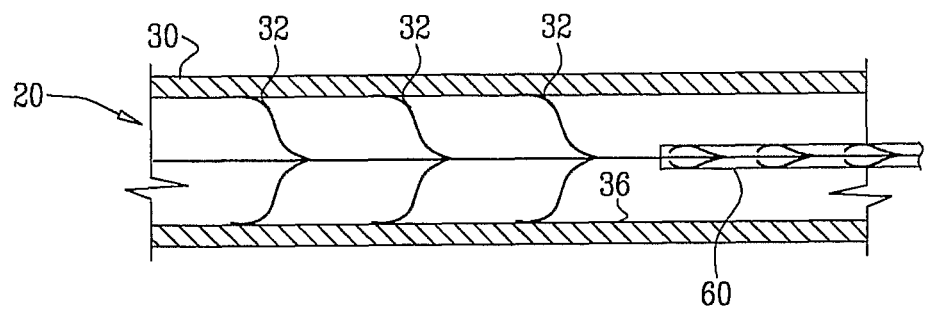
FIG. 4 is a schematic illustration of yet another configuration of the electrode device of FIG. 1, in accordance with an embodiment of the present invention.

FIG. 4 is a schematic illustration of yet another configuration of electrode device 20, in accordance with an embodiment of the present invention. In this embodiment, electrodes 32 are configured to expand into contact with wall 36 of blood vessel 30. Electrodes 32 are inserted into blood vessel 30 using a catheter 60. The electrodes are stored in the catheter in a contracted position. After the catheter has been advanced to a desired location in the blood vessel, the catheter is withdrawn from the blood vessel, exposing the electrodes and allowing them to expand against the wall of the blood vessel. For some applications, catheter 60 is additionally used to remove electrodes 32 from blood vessel 30 after treatment. The catheter is advanced over the electrodes, causing the electrodes to contract and be stored in the catheter. The catheter, holding the electrodes, is then withdrawn from the blood vessel. Alternatively, the electrodes are withdrawn without using the catheter, because their orientation within the blood vessel allows them to be freed from their contact points with the blood vessel by pulling the lead connecting the electrodes.

In an embodiment of the present invention, control unit 34 is adapted to drive only a portion of electrodes 32 at any given time. For some applications, control unit 34 drives only a portion of the electrodes by sending a multiplexed signal to all of the electrodes over a set of wires. For example, control unit 34 may use time-division, frequency-division, or digital multiplexing. To enable such multiplexing, each electrode typically comprises a microchip that interprets whether the signal generated by control unit 20 is intended to cause the electrode to apply a current to tissue in its vicinity. The use of these multiplexing techniques typically allows the use of only a few (e.g., 3-4) wires to control all of the electrodes.

Reference is now made to FIGS. 1-4. For some applications, control unit 34 is adapted to configure the signal applied by electrodes 32 to have one or both of the following parameters: a frequency of between about 3 and about 20 Hz (e.g., between about 5 and about 10 Hz), and/or a voltage less than about 5 V. For some applications, the signal is monophasic, while for other applications the signal is biphasic. For some applications, the control unit applies the signal having a duty cycle (e.g., about 1-15%, or about 15-50%).

In an embodiment of the present invention, all or a portion of electrode device 20 is biodegradable, and is adapted to degrade after remaining in blood vessel 30 for a certain period of time. For some applications, only the portions of electrode device 20 that are placed in blood vessel 30 are biodegradable, while control unit 34 is not biodegradable. In an embodiment, the portions of electrode device 20 in blood vessel 30 comprise a biodegradable carbon polymer or a biodegradable sugar polymer. As appropriate, one or both of these polymers has metal particles dispersed therein in order to provide suitable electrode properties.

Reference is again made to FIG. 1. For some applications, control unit 34 is coupled to electrode device 20 over wires 38. Control unit 34 is implanted in the body of the subject outside blood vessel 30, or is positioned external to the body of the subject. For other applications control unit 34 is wirelessly coupled to electrode device 20, for wireless transmission of energy and/or data. For example, the control unit may be inductively coupled to the electrode device, or the control unit may comprise an ultrasonic transducer that transmits energy to the electrode device, which receives the energy using an ultrasonic transducer, such as a piezoelectric transducer. For some applications, stent 40 itself serves as an antenna for receiving inductive energy and/or a wireless data signal from control unit 34. Control unit 34 comprises a power source, such as a battery, or a galvanic power source (in which case, separate ones of electrodes 32 may function as the anode and cathode of a galvanic cell).

In an embodiment of the present invention, electrode device 20 is configured to release a local or systemic drug into blood vessel 30, such as an anticoagulation agent (e.g., heparin), an immunosuppressive agent (e.g., sirolimus), a chemotherapy agent (e.g., taxol), a hormone (e.g., estradiol), or an NO-releasing compound.

In an embodiment of the present invention, electrode device 20 is adapted to be placed in direct contact with cardiac muscle of the subject, so as to induce an increase in NO secretion by the cardiac muscle.

In an embodiment of the present invention, electrode device 20 is adapted to be placed in contact with non-vascular smooth muscle (e.g., smooth muscle of the gastrointestinal tract).

In an embodiment of the present invention, electrode device 20 is adapted to be placed in an eye of a subject, and to induce dilation of a retinal artery, for example to treat diabetic retinopathy. For some applications, electrode device 20 comprises a small coil, which receives energy inductively in order to drive current into the tissue in contact therewith or adjacent thereto. The energy may be released by inductively driving current flow in the tissue, or via an electrode coupled to the coil. As appropriate based on surgical constraints or the particular pathology to be treated, the coil may be placed in an anterior or posterior position within the globe of the eye, or, alternatively, posterior to the retina.

In an embodiment of the present invention, one or more electrodes are placed in or adjacent to the subject's eye, and are driven to apply a signal that induces NO production adjacent to the electrodes, in order to treat an eye disease. For example, the increased NO production may be used to reduce intraocular pressure, in order to treat glaucoma. Alternatively or additionally, increased blood flow induced by the NO production minimizes optic nerve degeneration, such as is seen in age-related macular degeneration (AMD). Alternatively or additionally, as noted hereinabove, the increased blood flow in one or more retinal arteries treats or prevents diabetic retinopathy.

In an embodiment of the present invention, a system for treating glaucoma comprises one or more electrodes (e.g., exactly two electrodes) which are adapted to placed around a cornea of the eye, and a control unit which drives the electrodes to apply a signal that induces NO production in a vicinity of the trabecular meshwork of the eye. Such NO production enhances the flow of aqueous humour through the trabecular meshwork to Schlemm's canal, thereby reducing intraocular pressure to treat glaucoma.

For some applications, the control unit is configured (including being sufficiently small) to be placed in the eye, and the system comprises a photovoltaic cell that is configured to power the control unit.

In an embodiment of the present invention, electrode device 20 is used to apply electrical stimulation during the process of deriving blood vessels (i.e., veins or arteries) from stem cells, such as from embryonic stem cells. Alternatively or additionally, electrode device 20 is used to apply electrical stimulation to blood vessels derived from stem cells after the blood vessels have been implanted in a subject. An increase in NO production caused by such stimulation may be beneficial for the blood vessels, e.g., may aid the process of differentiating the stem cells into the blood vessels. These stimulation techniques may be used, for example, in conjunction with techniques for differentiating stem cells into blood vessels described in the above-mentioned article by Levenberg S et al.

Figure 5:
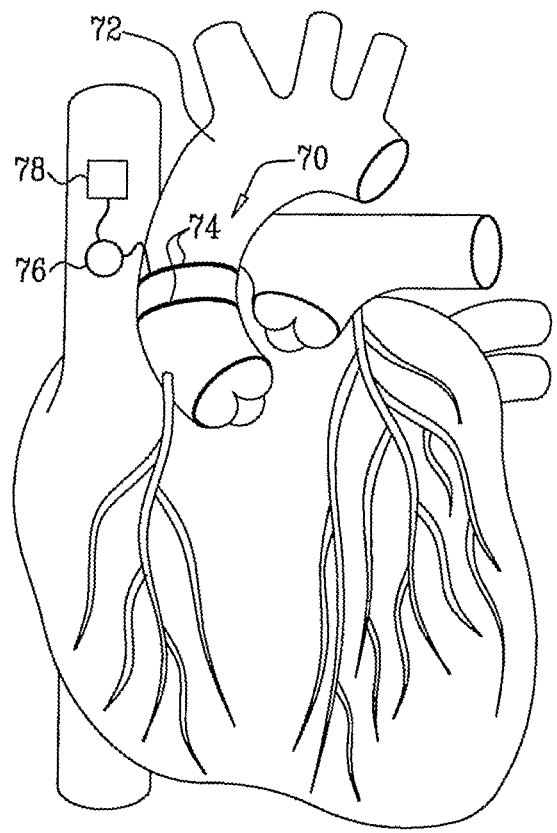
FIG. 5 is a schematic illustration of a counterpulsation device inserted in an ascending aorta of a subject, in accordance with an embodiment of the present invention.

Reference is made to FIG. 5, which is a schematic illustration of a counterpulsation device 70 inserted in an ascending aorta 72 of a subject, in accordance with an embodiment of the present invention. FIG. 5 shows insertion into ascending aorta 72 by way of illustration and not limitation, and the scope of the present invention includes, alternatively or additionally, inserting device 70 into the descending aorta. Additionally, it is noted that the size of device 70 may be considerably longer than as shown in FIG. 5 (e.g., 5-15 cm, or 15-30 cm), depending on the extent of the counterpulsation effect that is desired.

Counterpulsation device 70 comprises one or more electrodes 74, and an implantable or external control unit 76. Control unit 76 is adapted to drive electrodes 74 to apply an electrical signal to a wall of ascending aorta 72 during systole, and to configure the signal to induce an increase in NO secretion by the wall. The increased NO secretion dilates the wall such that during systole the wall stores energy, and pressure on the heart is reduced. During diastole, the wall constricts, releasing the stored energy and thereby increasing blood pressure and coronary blood flow. For some applications, control unit 76 is additionally configured to drive electrodes 74 to apply, during diastole, stimulation configured to enhance the rapid constriction of aorta 72.

In an embodiment, electrodes 74 are driven to apply a signal during systole that is about 1-10 mA (e.g., about 1-7 mA, or about 4-10 mA, typically about 4-5 mA) at about 1-30 Hz (e.g., about 1-20 Hz, or about 10-30 Hz, typically about 10 Hz). For some applications, the signal applied during diastole has an amplitude and/or a signal frequency that is between about 1.5 and 4 times the corresponding value during systole. In an embodiment, electrodes 74 are driven to apply a signal during diastole that is about 5-20 mA (e.g., about 10 mA) at a frequency that is between about 15 and 100 Hz, e.g., about 50 Hz.

For some applications, counterpulsation device 70 is about 25 cm long, and induces a 10% dilation of aorta 72 and, in turn, an approximately 40 cc increase in volume along 25 cm of the aorta. For some applications, counterpulsation device 70 is used to treat a subject suffering from congestive heart failure (CHF), while for other applications, the device is used to treat non-CHF subjects, such as subjects suffering from high systolic blood pressure.

For some applications, counterpulsation device 70 comprises at least one physiological sensor 78, such as an electrocardiogram (ECG) monitor, or a pressure sensor. Control unit 76 determines the one or more parameters of the signal application (such as a timing parameter) responsively to a sensor signal generated by sensor 78. For some applications, control unit 76 is adapted to drive electrodes 74 to apply the signal every heart beat, while for other applications the signal is applied less than every heartbeat, such as once every several heartbeats. For some applications, the control unit is configured to drive the electrodes to begin application of the systolic signal slightly prior to the beginning of systole (e.g., less than 50 ms prior to the beginning of systole), which generally enhances the induced dilation of the aorta.

For some applications, counterpulsation device 70 alternatively or additionally comprises an element configured to mechanically dilate ascending aorta 72 (or the descending aorta) during at least a portion of systole, by causing the aorta to assume a more elliptical shape. For some applications, the element is placed within the aorta, while for other applications the element is placed outside the aorta. For example, the element may comprise one or more magnets and/or coils, which are driven to change the shape of the element using electricity, piezoelectric elements, and/or hydraulic pressure. For some applications, the element both applies the mechanical force and functions as one or more of electrodes 74. For applications in which both the electrical signal and mechanical force is applied during systole, the counterpulsation effect is intensified by the combination of the electrically-induced dilation, the mechanically-induced change in cross-sectional shape, and the natural expansion of the aorta during systole.

For some applications, counterpulsation device 70 is applied to an artery other than an aorta.

Figure 6:
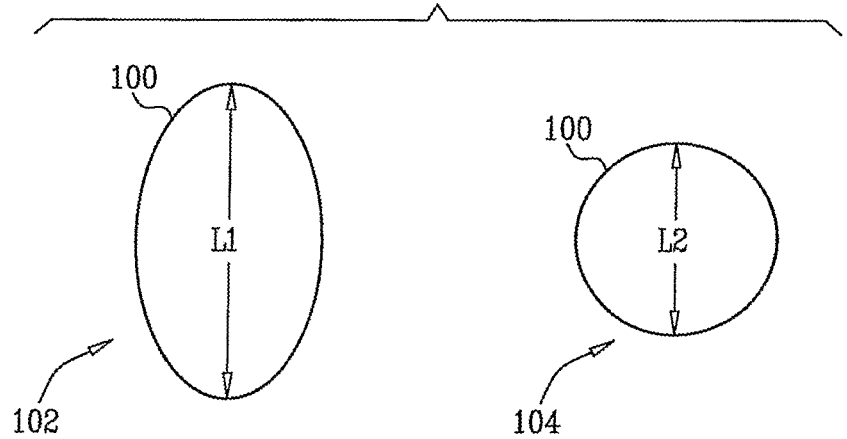
FIG. 6 is a schematic cross-sectional illustration of an artificial artery, in accordance with an embodiment of the present invention.

Reference is made to FIG. 6, which is a schematic cross-sectional illustration of an artificial artery 100, in accordance with an embodiment of the present invention. Artificial artery 100 is typically used as a graft for a coronary bypass procedure. For some applications, artificial artery 100 has a diameter of less than 7 mm, such as less than 5 mm or less than 3 mm. Artificial artery 100 is configured to assume a first cross-sectional shape 102 during a first phase of a cardiac cycle (e.g., systole or diastole), and a second cross-sectional shape 104 during a second phase of the cardiac cycle (e.g., diastole or systole). Typically, one or both of the cross-sectional shapes are elliptical, and have major axes with different lengths L1 and L2, respectively. For some applications, one of the cross-sectional shapes is substantially circular. For some applications, a ratio of L1 to L2 is greater than 1.1, 1.2, 1.3, 1.4, or 1.5. Such shape changing during each cardiac cycle generally reduces the likelihood of artificial artery 100 becoming blocked over time. Without wishing to be bound by any particular theory, the inventor hypothesizes that the frequent shape changes of arteries in skeletal muscle, caused by movement of the muscle, may help prevent blockage of these arteries. The shape changes of artificial artery 100 may have the same general beneficial effect.

In an embodiment of the present invention, an electrode device comprises one or more electrodes. The electrode device is configured to be placed outside of a blood vessel, such as an artery, in a vicinity of the blood vessel, such that the electrodes remain outside the blood vessel in electrical communication with the blood vessel. An implantable or external control unit is configured to drive the electrodes to apply an electrical signal to the blood vessel, and to configure the signal to induce an increase in nitric oxide (NO) secretion by a wall of the blood vessel. For some applications, the electrode device comprises a plurality of electrodes, and the control unit is configured to randomly or quasi-randomly activate a subset of the electrodes, and repeatedly change which electrodes are in the subset. For some applications, the electrode device is shaped as a tube having an inner surface to which the electrodes are coupled. For some applications, the electrode device comprises at least one elongated lead, which is configured to be placed in the blood vessel, and to serve as an electrode having a polarity opposite that of the electrodes outside the blood vessel.

In an embodiment of the present invention, a system comprises an electrode device and an implantable or external control unit. The electrode device comprises one or more electrodes configured to be placed in or outside a blood vessel in a vicinity of a baroreceptor. The control unit drives the electrodes to apply to the blood vessel an electrical signal that induces NO secretion by a wall of the artery. Such NO secretion causes dilation of the wall of the blood vessel, thereby activating the baroreceptor. For some applications, the system comprises a sensor for sensing a feature of a cardiac cycle, and the control unit is configured to synchronize the signal application with the feature. For example, the control unit may be configured to apply the signal once per heart beat, or every nth heart beat, such as every second or third heart beat. For some applications, the control unit applies the signal only during systole. For some applications, the system comprises a blood pressure sensor, and the control unit drives the electrode device to apply the signal responsively to a sensed blood pressure. For example, the blood vessel may be the carotid artery or the aorta in a vicinity of the aortic arch.

Alternatively or additionally, the system comprises an element configured to mechanically dilate the blood vessel in the vicinity of the baroreceptor, such as during systole, as described above. For some applications, the element is placed within the blood vessel, while for other applications the element is placed outside the blood vessel. For example, the element may comprise one or more magnets and/or coils, which are driven to change the shape of the element using electricity, piezoelectric elements, and/or hydraulic pressure. For some applications, the element is configured to store energy during one phase of the cardiac cycle, and use the stored energy to change the shape of the element during another phase of the cardiac cycle. For some applications, the element for applying the mechanical force also serves as one or more of the electrodes.

For some applications, the element is configured to cause the cross-sectional shape of the blood vessel to be more elliptical during diastole than the shape would otherwise be (it being noted that rigid blood vessels generally have a substantially circular cross-sectional shape). As a result, the baroreceptor typically detects more shape change during systole that it otherwise would. For example, the element may be configured to function as a weak spring in order to change the cross-sectional shape.

In an embodiment of the present invention, a treatment method comprises removing plaque from an artery in a vicinity of a baroreceptor, in order to increase flexibility of the artery and thus sensitivity of the baroreceptor. For example, the SilverHawk™ Plaque Excision System (FoxHollow Technologies, Inc., Redwood City, Calif.) may be used to remove the plaque.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a bifurcation stent comprising one or more electrodes, the stent configured to be placed in a primary passage and a secondary passage of a blood vessel; and
a control unit, configured to drive the electrodes to apply a signal to a wall of the blood vessel, and to configure the signal to increase nitric oxide (NO) secretion by the wall,
wherein the blood vessel includes an artery and wherein the control unit is configured to drive the electrodes to apply counterpulsation to the artery, by:
driving the electrodes to apply a systolic electrical signal to a wall of the artery during at least a commencement of systole of a cardiac cycle of the subject,
configuring the systolic signal to induce an increase in nitric oxide (NO) secretion by the wall, such that during at least the commencement of systole, the artery stores energy by the wall of the artery dilating, and
withholding the electrodes from the systolic signal to the wall during at least a portion of diastole of the subject's cardiac cycle, such that during the at least a portion of diastole the wall of the artery releases the stored energy.

2. Apparatus for applying counterpulsation to an artery of a subject, the apparatus comprising:
one or more electrodes, adapted to be placed in a vicinity of the artery; and
a control unit, configured to apply the counterpulsation to the artery, by:
driving the electrodes to apply a systolic electrical signal to a wall of the artery during at least a commencement of systole of a cardiac cycle of the subject,
configuring the systolic signal to induce an increase in nitric oxide (NO) secretion by the wall, such that during at least the commencement of systole, the artery stores energy by the wall of the artery dilating, and
withholding the electrodes from applying the systolic signal to the wall during at least a portion of diastole of the subject's cardiac cycle, such that during the at least a portion of diastole the wall of the artery releases the stored energy.

3. The apparatus according to claim 2, comprising a physiological sensor, which is configured to generate a sensor signal, wherein the control unit is configured to set at least one parameter of the systolic signal responsively to the sensor signal.

4. The apparatus according to claim 2, wherein the control unit is configured to drive the electrodes to begin application of the systolic signal slightly prior to a commencement of systole.

5. The apparatus according to claim 2, wherein the control unit is configured to drive the electrodes to begin application of the systolic signal less than 50 ms prior to a commencement of systole.

6. The apparatus according to claim 2, wherein the control unit is adapted to configure the systolic signal to have an amplitude of between 1 and 10 mA.

7. The apparatus according to claim 2, wherein the control unit is adapted to configure the systolic signal to have a frequency of less than 30 Hz.

8. The apparatus according to claim 2, wherein the control unit is adapted to drive the electrodes to apply a diastolic electrical signal to the wall during at least a portion of diastole, and to configure the diastolic signal to enhance constriction of the artery during diastole.

9. The apparatus according to claim 8, wherein the control unit is adapted to configure a diastolic value of a parameter of the diastolic signal to be between 1.5 and 4 times a systolic value of the parameter of the systolic signal, the parameter selected from the group consisting of: an amplitude, and a frequency.

10. The apparatus according to claim 8, wherein the control unit is adapted to configure the diastolic signal to have an amplitude of between 5 and 20 mA.

11. The apparatus according to claim 8, wherein the control unit is adapted to configure the diastolic signal to have a frequency of between 15 and 100 Hz.

12. The apparatus according to claim 8, wherein the control unit is configured to drive the electrodes to apply the diastolic electrical signal to the wall of the artery by driving the electrodes to apply a biphasic diastolic signal to the wall of the artery.

13. The apparatus according to claim 2, further comprising an element configured to mechanically dilate the artery.

14. The apparatus according to claim 13, wherein the element is configured to mechanically dilate the artery during at least a portion of systole.

15. The apparatus according to claim 14, wherein the element is configured to be placed at least partially in the artery.

16. The apparatus according to claim 14, wherein the element is configured to be placed at least partially outside the artery.

17. The apparatus according to claim 14, wherein the element is configured to serve as at least one of the one or more electrodes.

18. The apparatus according to claim 13, wherein the element is configured to be placed at least partially in the artery.

19. The apparatus according to claim 13, wherein the element is configured to be placed at least partially outside the artery.

20. The apparatus according to claim 13, wherein the element is configured to serve as at least one of the one or more electrodes.

21. The apparatus according to claim 13, wherein the element configured to dilate the artery comprises a magnet.

22. The apparatus according to claim 13, wherein the element configured to dilate the artery comprises a coil.

23. The apparatus according to claim 13, wherein the element configured to dilate the artery comprises a piezoelectric element.

24. The apparatus according to claim 13, wherein the element is configured to dilate the artery using electricity.

25. The apparatus according to claim 13, wherein the element is configured to dilate the artery using hydraulic pressure.

26. The apparatus according to claim 2, wherein the artery includes a coronary artery of the subject and wherein the one or more electrodes are configured to be placed in a vicinity of the coronary artery.

27. The apparatus according to claim 2, wherein the artery includes an aorta of the subject and wherein the one or more electrodes are configured to be placed in a vicinity of the aorta.

28. The apparatus according to claim 27, wherein the aorta includes an ascending aorta of the subject and wherein the one or more electrodes are configured to be placed in a vicinity of the ascending aorta.

29. The apparatus according to claim 27, wherein the aorta includes a descending aorta of the subject and wherein the one or more electrodes are configured to be placed in a vicinity of the descending aorta.

30. The apparatus according to claim 2, wherein, at at least one time, the control unit is configured to drive only a portion of the electrodes.

31. The apparatus according to claim 30, wherein the control unit is configured to activate the electrodes in a sequence by time dividing activation of the electrodes.

32. The apparatus according to claim 2, wherein the control unit is configured drive the electrodes to apply the systolic electrical signal to the wall of the artery by driving the electrodes to apply a biphasic systolic signal to the wall of the artery.

33. A method comprising:
placing a bifurcation stent including one or more electrodes in a primary passage and a secondary passage of a blood vessel;
driving the electrodes to apply a signal to a wall of the blood vessel; and
configuring the signal to increase nitric oxide (NO) secretion by the wall,
wherein the blood vessel includes an artery, the method comprising applying counterpulsation to the artery, by:
driving the electrodes to apply a systolic electrical signal to a wall of the artery during at least a commencement of systole of a cardiac cycle of the subject;
configuring the systolic signal to induce an increase in nitric oxide (NO) secretion by the wall, such that during at least the commencement of systole, the artery stores energy by the wall of the artery dilating; and
withholding applying the systolic signal to the wall during at least a portion of diastole of the subject's cardiac cycle, such that during the at least a portion of diastole the wall of the artery releases the stored energy.

34. A method for applying counterpulsation to an artery of a subject, the method comprising:
applying a systolic electrical signal to a wall of the artery during at least a commencement of systole of a cardiac cycle of the subject;
configuring the systolic signal to induce an increase in nitric oxide (NO) secretion by the wall, such that during at least the commencement of systole, the artery stores energy by the wall of the artery dilating; and
withholding applying the systolic signal to the wall during at least a portion of diastole of the subject's cardiac cycle, such that during the at least a portion of diastole the wall of the artery releases the stored energy.

35. The method according to claim 34, wherein applying the systolic signal comprises sensing a physiological parameter of the subject, and setting at least one parameter of the systolic signal responsively to the sensed physiological parameter.

36. The method according to claim 34, wherein applying the systolic signal comprises beginning applying the systolic signal less than 50 ms prior to a commencement of systole.

37. The method according to claim 34, wherein applying the systolic signal comprises configuring the systolic signal to have an amplitude of between 1 and 10 mA.

38. The method according to claim 34, applying the systolic signal comprises configuring the systolic signal to have a frequency of less than 30 Hz.

39. The method according to claim 34, comprising applying a diastolic electrical signal to the wall during at least a portion of diastole, and configuring the diastolic signal to enhance constriction of the artery during diastole.

40. The method according to claim 39, wherein applying the diastolic signal comprises configuring a diastolic value of a parameter of the diastolic signal to be between 1.5 and 4 times a systolic value of the parameter of the systolic signal, the parameter selected from the group consisting of: an amplitude, and a frequency.

41. The method according to claim 39, wherein applying the diastolic signal comprises configuring the diastolic signal to have an amplitude of between 5 and 20 mA.

42. The method according to claim 39, applying the diastolic signal comprises configuring the diastolic signal to have a frequency of between 15 and 100 Hz.

43. The method according to claim 39, wherein applying the diastolic electrical signal comprises applying a biphasic diastolic signal.

44. The method according to claim 34, further comprising mechanically dilating the artery.

45. The method according to claim 44, wherein mechanically dilating the artery comprises mechanically dilating the artery during at least a portion of systole.

46. The method according to claim 45, wherein mechanically dilating the artery comprises mechanically dilating the artery from within the artery.

47. The method according to claim 45, wherein mechanically dilating the artery comprises mechanically dilating the artery from outside the artery.

48. The method according to claim 44, wherein mechanically dilating the artery comprises mechanically dilating the artery from within the artery.

49. The method according to claim 44, wherein mechanically dilating the artery comprises mechanically dilating the artery from outside the artery.

50. The method according to claim 44, wherein mechanically dilating the artery comprises mechanically dilating the artery using an electrode.

51. The method according to claim 44, wherein dilating the artery comprises dilating the artery with a magnet.

52. The method according to claim 44, wherein dilating the artery comprises dilating the artery with a coil.

53. The method according to claim 44, wherein dilating the artery comprises dilating the artery with a piezoelectric element.

54. The method according to claim 44, wherein dilating the artery comprises dilating the artery using electricity.

55. The method according to claim 44, wherein dilating the artery comprises dilating the artery using hydraulic pressure.

56. The method according to claim 30, wherein the artery includes a coronary artery of the subject and wherein applying the systolic electrical signal to the wall of the artery comprises applying the systolic electrical signal to a wall of the coronary artery.

57. The method according to claim 30, wherein the artery includes an aorta of the subject and wherein applying the systolic electrical signal to the wall of the artery comprises applying the systolic electrical signal to a wall of the aorta.

58. The method according to claim 57, wherein the aorta includes an ascending aorta of the subject, and wherein applying the systolic electrical signal to the wall of the aorta comprises applying the systolic electrical signal to a wall of the ascending aorta.

59. The method according to claim 57, wherein the aorta includes a descending aorta of the subject, and wherein applying the systolic electrical signal to the wall of the aorta comprises applying the systolic electrical signal to a wall of the descending aorta.

60. The method according to claim 30, wherein applying the systolic electrical signal comprises applying the systolic electrical signal through a plurality of electrodes, and, at at least one time, applying the systolic electrical signal via a first portion of the electrodes and not via a second portion of the electrodes.

61. The method according to claim 60, wherein applying the systolic electrical signal comprises activating a set electrodes in a sequence by time dividing activation of the electrodes.

62. The method according to claim 34, wherein applying the systolic electrical signal comprises applying a biphasic systolic signal.

63. Apparatus comprising:
one or more electrodes configured to be placed on a wall of a blood vessel; and
a control unit, configured to reduce platelet aggregation in a vicinity of the blood vessel wall by driving the electrodes to apply a signal to the blood vessel wall and by configuring the signal to increase nitric oxide (NO) secretion by the wall,
wherein the blood vessel includes an artery and wherein the control unit is further configured to apply counterpulsation to the artery, by:
driving the electrodes to apply a systolic electrical signal to a wall of the artery during at least a commencement of systole of a cardiac cycle of the subject,
configuring the systolic signal to induce an increase in nitric oxide (NO) secretion by the wall, such that during at least the commencement of systole, the artery stores energy by the wall of the artery dilating, and
withholding the electrodes from applying the systolic signal to the wall during at least a portion of diastole of the subject's cardiac cycle, such that during the at least a portion of diastole the wall of the artery releases the stored energy.

64. Apparatus comprising:
one or more electrodes configured to be placed in a vicinity of a blood vessel bifurcation; and
a control unit, configured to drive the electrodes to apply a signal to a wall of the blood vessel in the vicinity, and to configure the signal to increase nitric oxide (NO) secretion by the wall,
wherein the blood vessel includes an artery and wherein the control unit is configured to drive the electrodes to apply counterpulsation to the artery, by:
driving the electrodes to apply a systolic electrical signal to a wall of the artery during at least a commencement of systole of a cardiac cycle of the subject,
configuring the systolic signal to induce an increase in nitric oxide (NO) secretion by the wall, such that during at least the commencement of systole, the artery stores energy by the wall of the artery dilating, and
withholding the electrodes from the systolic signal to the wall during at least a portion of diastole of the subject's cardiac cycle, such that during the at least a portion of diastole the wall of the artery releases the stored energy.

65. The apparatus according to claim 64, wherein the control unit is configured to reduce platelet aggregation in the vicinity of the bifurcation by increasing the NO secretion.

66. A method comprising:
placing one or more electrodes inside a blood vessel;
driving the electrodes to apply a signal to a wall of the blood vessel; and
reducing platelet aggregation inside the blood vessel by configuring the signal to increase nitric oxide (NO) secretion by the wall,
wherein the blood vessel includes an artery, the method further comprising applying counterpulsation to the artery, by:
driving the electrodes to apply a systolic electrical signal to a wall of the artery during at least a commencement of systole of a cardiac cycle of the subject;
configuring the systolic signal to induce an increase in nitric oxide (NO) secretion by the wall, such that during at least the commencement of systole, the artery stores energy by the wall of the artery dilating; and
withholding applying the systolic signal to the wall during at least a portion of diastole of the subject's cardiac cycle, such that during the at least a portion of diastole the wall of the artery releases the stored energy.

67. A method comprising:
placing one or more electrodes in a primary passage and a secondary passage of a blood vessel;
driving the electrodes to apply a signal to a wall of the blood vessel; and
reducing platelet aggregation inside the blood vessel by configuring the signal to increase nitric oxide (NO) secretion by the wall, wherein the blood vessel includes an artery, the method further comprising applying counterpulsation to the artery, by:
- driving the electrodes to apply a systolic electrical signal to a wall of the artery during at least a commencement of systole of a cardiac cycle of the subject;
- configuring the systolic signal to induce an increase in nitric oxide (NO) secretion by the wall, such that during at least the commencement of systole, the artery stores energy by the wall of the artery dilating; and
- withholding applying the systolic signal to the wall during at least a portion of diastole of the subject's cardiac cycle, such that during the at least a portion of diastole the wall of the artery releases the stored energy.

68. Apparatus, comprising:
- one or more electrodes, adapted to be placed in a vicinity of a blood vessel; and
- a control unit, configured to:
    - drive the electrodes to apply an electrical signal to a wall of the blood vessel, the electrical signal having an amplitude of 1-10 mA, and
    - configure the signal to dilate the blood vessel by inducing an increase in nitric oxide secretion by the wall,
- wherein the blood vessel includes an artery and wherein the control unit is configured to apply counterpulsation to the artery, by:
    - driving the electrodes to apply a systolic electrical signal to a wall of the artery during at least a commencement of systole of a cardiac cycle of the subject,
    - configuring the systolic signal to induce an increase in nitric oxide (NO) secretion by the wall, such that during at least the commencement of systole, the artery stores energy by the wall of the artery dilating, and
    - withholding the electrodes from applying the systolic signal to the wall during at least a portion of diastole of the subject's cardiac cycle, such that during the at least a portion of diastole the wall of the artery releases the stored energy.

69. A method, comprising:
- applying an electrical signal to a wall of a blood vessel, the signal having an amplitude of 1-10 mA; and
- configuring the signal to dilate the blood vessel by inducing an increase in nitric oxide secretion by the wall,
- wherein the blood vessel includes an artery, the method comprising applying counterpulsation to the artery, by:
    - driving electrodes to apply a systolic electrical signal to a wall of the artery during at least a commencement of systole of a cardiac cycle of the subject;
    - configuring the systolic signal to induce an increase in nitric oxide (NO) secretion by the wall, such that during at least the commencement of systole, the artery stores energy by the wall of the artery dilating; and
    - withholding applying the systolic signal to the wall during at least a portion of diastole of the subject's cardiac cycle, such that during the at least a portion of diastole the wall of the artery releases the stored energy.

* * * * *